US009629592B2

(12) United States Patent
Lee et al.

(10) Patent No.: US 9,629,592 B2
(45) Date of Patent: Apr. 25, 2017

(54) X-RAY PHOTOGRAPHING APPARATUS (71) Applicant: GENERAL ELECTRIC COMPANY, Schenectady, NY (US)

(72) Inventors: Chang Hwa Lee, Hwaseong (KR); Min Ho Son, Hwaseong (KR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/758,188

(22) PCT Filed: Dec. 26, 2013

(86) PCT No.: PCT/KR2013/012180
§ 371 (c)(1),
(2) Date: Jun. 26, 2015

(87) PCT Pub. No.: WO2014/104745
PCT Pub. Date: Jul. 3, 2014

(65) Prior Publication Data
US 2015/0359495 A1 Dec. 17, 2015

(30) Foreign Application Priority Data
Dec. 27, 2012 (KR) .................. 10-2012-0155160

(51) Int. Cl.
*A61B 6/00* (2006.01)
*A61B 6/04* (2006.01)

(52) U.S. Cl.
CPC ............. *A61B 6/4291* (2013.01); *A61B 6/44* (2013.01); *A61B 6/502* (2013.01); *A61B 6/0414* (2013.01)

(58) Field of Classification Search
USPC ................... 378/145, 146, 154, 155
See application file for complete search history.

(56) References Cited

U.S. PATENT DOCUMENTS

| 2,689,916 A | 9/1954 | Lohman et al. |
| 2,938,120 A | 5/1960 | Forsyth |
| 2010/0303202 A1 | 12/2010 | Ren et al. |
| 2013/0259192 A1 | 10/2013 | Ren et al. |

FOREIGN PATENT DOCUMENTS

| DE | 637579 | 1/1937 |
| FR | 1147221 | 11/1957 |
| JP | S51-127273 U | 10/1976 |
| JP | H01-225938 A | 9/1989 |
| JP | 2001-333895 A | 12/2001 |

(Continued)

OTHER PUBLICATIONS

Extended European Search Report for European Patent Application No. 13869712.3 dated Nov. 27, 2015.

(Continued)

*Primary Examiner* — Nicole Ippolito
*Assistant Examiner* — Hanway Chang (57) ABSTRACT

Disclosed herein is an X-ray photographing apparatus. The X-ray photographing apparatus uses a moving source and a tension spring in order to let a grid reciprocate for removing a scattered radiation. The moving source generates moving force moving the grid toward one side, and the tension spring applies tension force moving the grid toward the other side. According to the present invention, since the grid moves at a velocity close to a constant velocity, image quality is improved.

6 Claims, 7 Drawing Sheets

(56) References Cited

FOREIGN PATENT DOCUMENTS

| JP | 2003-185755 A | 7/2003 |
| JP | 2005-270396 A | 10/2005 |
| JP | 2012-235959 A | 12/2012 |
| KR | 10-2011-0063659 A | 6/2011 |
| KR | 10-2011-0089134 A | 8/2011 |

OTHER PUBLICATIONS

International Search Report for PCT/KR2013/012180 filed on Dec. 26, 2013.

X-RAY PHOTOGRAPHING APPARATUS

TECHNICAL FIELD

The present invention relates to an X-ray photographing apparatus, and more particularly, to a detecting module for detecting an X-ray transmitted through a target to be photographed.

BACKGROUND ART

X-ray photographing has been performed in various medical fields for the purpose of inspection.

At the time of performing the X-ray photographing, a scattered radiation is generated when a radiated X-ray is transmitted through a medium.

The scattered radiation causes a decrease in an image contrast and an increase in noise. Therefore, it is preferable to detect only a primary radiation having useful image information.

Generally, an anti-scatter grid is used in order to allow the primary radiation to be transmitted and block (or attenuate) the scattered radiation. Korean Patent Laid-Open Publication No. 10-2011-0063659 or Korean Patent Laid-Open Publication No. 10-2011-0089134 has disclosed a technology of applying a grid to a mammography. Here, the mammography is an X-ray photographing apparatus used to detect breast cancer, lesion, and micro-calcification.

As disclosed in the patent laid publications mentioned above, the grid is positioned between a target to be photographed (for example, 'breast') and a detector. In addition, the grid reciprocates so as to appropriately perform a function thereof. The present invention relates to a reciprocating technology of the grid.

The related art for reciprocation of a grid 141 will be described with reference to a schematic plan view of FIG. 1.

A moving device 143 is required in order to let the grid 141 reciprocate.

The moving device 143 includes a pair of coupling members 143a and 143b, a guide shaft 143c, a moving source 143d, a pair of compression springs 143f-1 and 143f-2, and a pair of support members 143g and 143h.

The coupling members 143a and 143b include long guide holes $GH_1$ and $GH_2$ formed therein, respectively, in a movement direction (horizontal direction) (See an arrow) of the grid 141. Front ends of the coupling members 143a and 143b are coupled to the grid 141. In addition, one coupling member 143a has a coupling groove JS formed at a rear end thereof.

The guide shaft 143c has a pair of guide bars 143c-1 and 143c-2 long in a horizontal direction.

The guide bars 143c-1 and 143c-2 are inserted into the guide holes $GH_1$ and $GH_2$ of the coupling members 143a and 143b, respectively. Therefore, horizontal direction of the coupling members 143a and 143b is guided by the guide bars 143c-1 and 143c-2.

The moving source 143d includes a motor 143d-1 and a transfer member 143d-2.

The motor 143d-1 generates moving force of the coupling members 143a and 143b. In FIG. 1, the moving force is applied leftward.

The transfer member 143d-2 has a front end inserted into the coupling groove JS of the coupling member 143a and a rear end connected to the motor 143d-1. Therefore, the transfer member 143d-2 transfers the moving force generated in the motor 143d-1 to the coupling member 143a.

The compression springs 143f-1 and 143f-2 are installed in a form in which the guide bars 143c-1 and 143c-2 are inserted thereinto, respectively. These compression springs 143f-1 and 143f-2 apply elastic force to the coupling member 143a rightward.

The support frames 143g and 143h support a bottom surface of the grid 141.

Reciprocation of the grid 141 performed in the configuration as described above will be described.

The moving force generated by the motor 143d-1 is transferred to the coupling member 143a through the transfer member 143d-2. Therefore, the coupling members 143a and 143b and the grid 141 move leftward. In addition, the compression springs 143f-1 and 143f-2 are compressed. When the moving force from the motor 143d-1 subsequently disappears, the coupling members 143a and 143b and the grid 141 move rightward by elastic restoring force of the compression springs 143f-1 and 143f-2.

Meanwhile, it is preferable that the grid 141 moves at a velocity close to a constant velocity in order to obtain appropriate image quality.

However, the related art as described above has the following factors hindering the constant velocity movement of the grid 141.

First, lengths of the compression springs 143f-1 and 143f-2 are short due to a limitation in installation. Therefore, a deviation between early restoring force (restoring force at a point in time in which the compression springs are maximally compressed) and later restoring force (restoring force immediately before the grid returns to its original position) is large.

Second, the front end of the transfer member 143d-2 is inserted into the coupling groove JS of the coupling member 143a with a clearance interposed therebetween. Therefore, vibrations, noise, and the like, are instantaneously generated due to a backlash between the transfer member 143d-2 and the coupling member 143a at the early stage of generation of the moving force of the motor 143d-1.

Therefore, the grid 141 may not move at a constant velocity within a moving section (about 12 mm). In addition, when the transfer member 143d-2 strikes the coupling member 143a, vibrations and noise are generated.

In addition, in the mammography, the grid 141 may be stood to be inclined at a predetermined angle depending on a photographing angle of a breast. In this case, the support frames 143g and 143h may not stably support the grid 141.

DISCLOSURE

Technical Problem

A first object of the present invention is to provide a technology capable of allowing a grid to move at a velocity close to a constant velocity.

A second object of the present invention is to provide a technology capable of allowing support frames to always stably support a grid.

Technical Solution

According to an exemplary embodiment of the present invention, there is provided an X-ray photographing apparatus including: a generator irradiating an X-ray to a target to be photographed; and a detecting module detecting the X-ray transmitted through the target to be photographed, wherein the detecting module includes: a grid reciprocating between first and second positions; a detector detecting the X-ray transmitted through the grid; and a moving device letting the grid reciprocate, the moving device including: a moving source providing moving force for moving the grid from the first position to the second position; and a tension spring providing tension force for moving the grid from the second position to the first position.

The moving device may further include: a coupling member connecting the moving source and the grid to each other so as to transfer the moving force of the moving source to the grid; and a guide shaft having a guide part guiding reciprocation of the coupling member, and the tension spring may have one side fixed to the coupling member and the other side fixed to the guide shaft.

The coupling member may have a coupling groove formed therein, and the moving device may further include: a motor generating moving force of the coupling member; a transfer member having a portion inserted into the coupling groove to transfer the moving force of the motor to the coupling member; and a pressing member giving pressure to the portion of the transfer member inserted into the coupling groove.

The moving device may further include at least one support frame provided with an insertion groove into which a portion of the grid is inserted so as to support the grid.

Advantageous Effects

According to the present invention, there are the following effects.

First, since the grid moves at a velocity close to a constant velocity, image quality is improved.

Second, since the support frames always stably support the grid, reliability of a product is improved.

Third, tapping sound between the transfer member and the coupling member is removed.

BEST MODE

Hereinafter, an exemplary embodiment of the present invention will be described.

For reference, for clearance of explanation, a description for overlapped portions or portions that are not associated with features of the present invention will be omitted or compressed.

Figure 2:
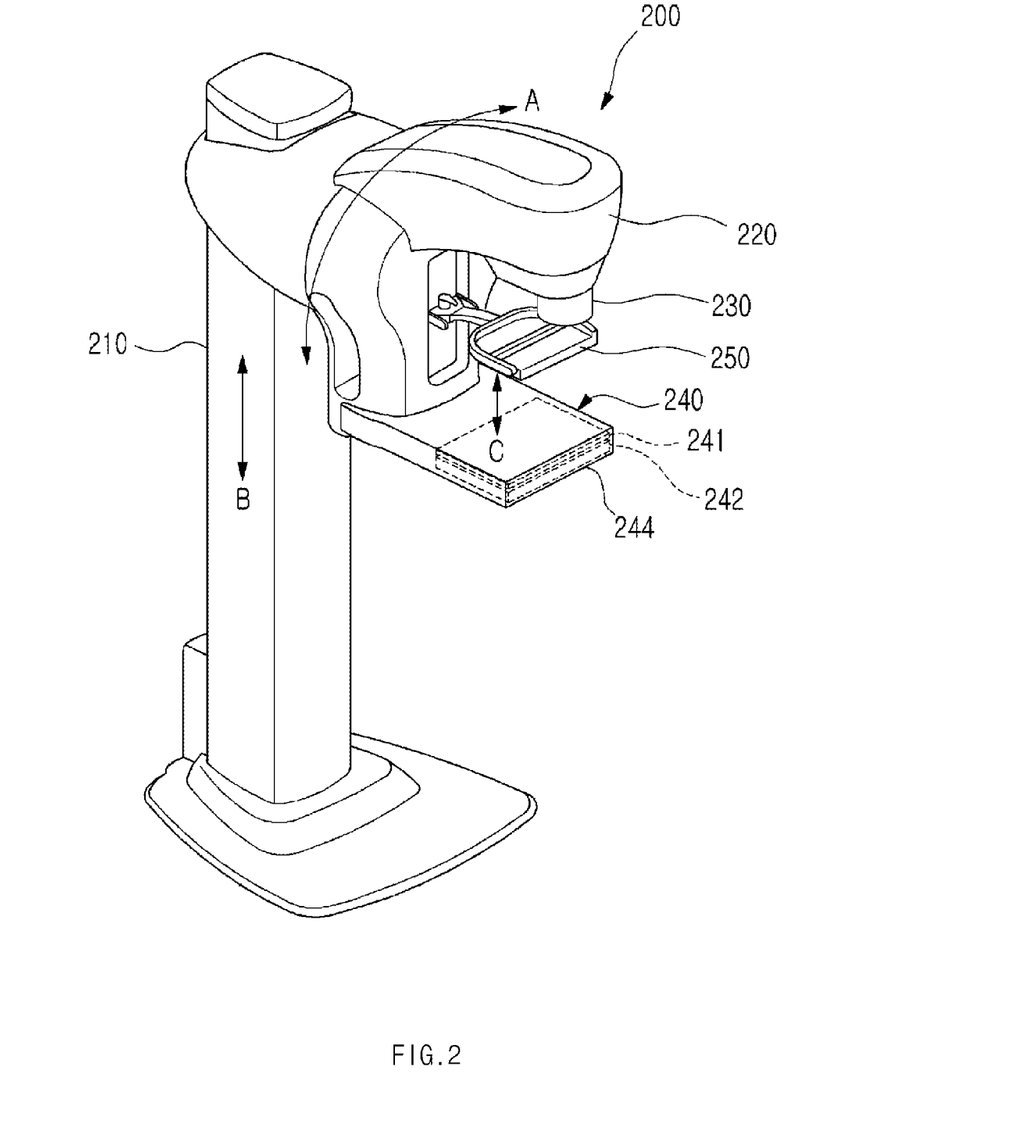
FIG. 2 is a perspective view of a mammography according to an exemplary embodiment of the present disclosure.

FIG. 2 is a perspective view of a mammography 200 according to an exemplary embodiment of the present disclosure.

The mammography 200 includes a column 210, a C arm 220, a generator 230, a detecting module 240, and a pressing member 250.

The column 210 supports the C arm 220.

The generator 230, the detecting module 240, and the pressing member 250 are installed in the C arm 220. The C arm 220 rotates (See an arrow A of FIG. 2) or ascends or descends (See an arrow B of FIG. 2) in a state in which it is supported by the column 210.

The generator 230 irradiates an X-ray toward the detecting module 240.

Figure 3:
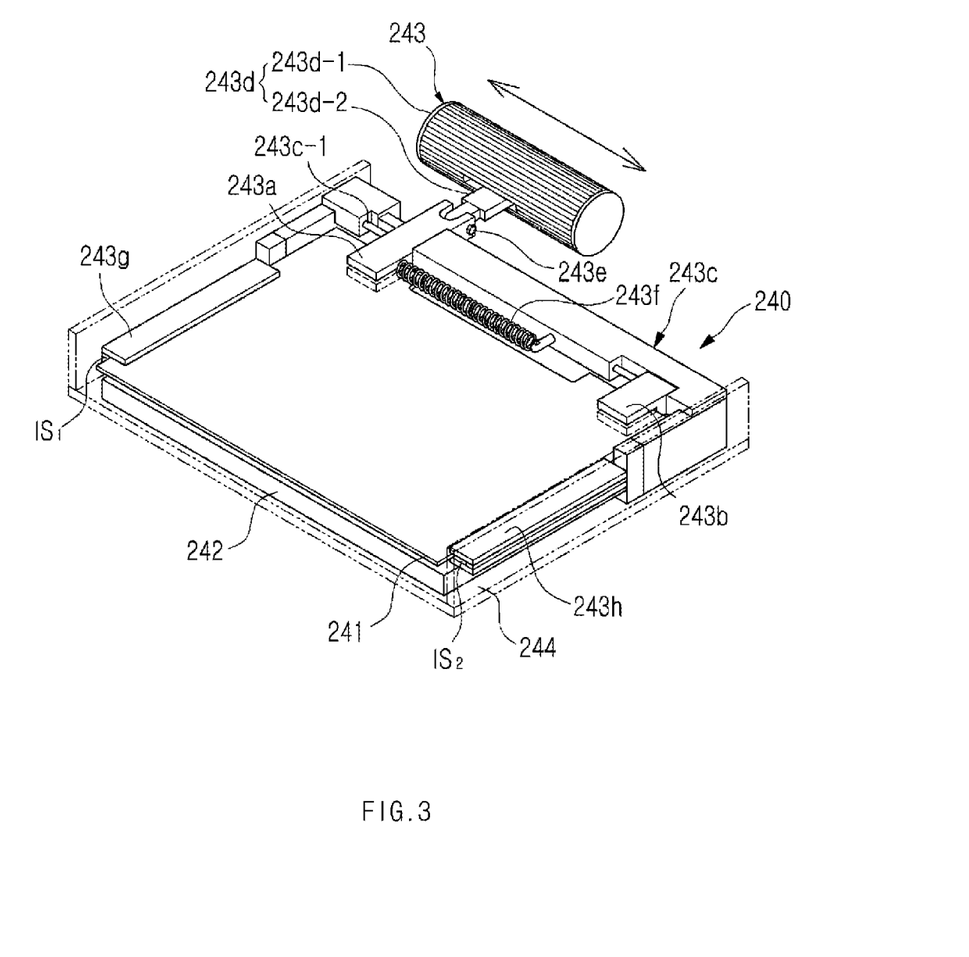
FIG. 3 is a schematic perspective view of main components of the mammography of FIG. 2.

The detecting module 240 detects an X-ray transmitted through a breast, which is a target to be photographed. FIG. 3 is a schematic perspective view of the detecting module 240, and FIGS. 4A and 4B are schematic plan views of the detecting module 240.

Figure 4:
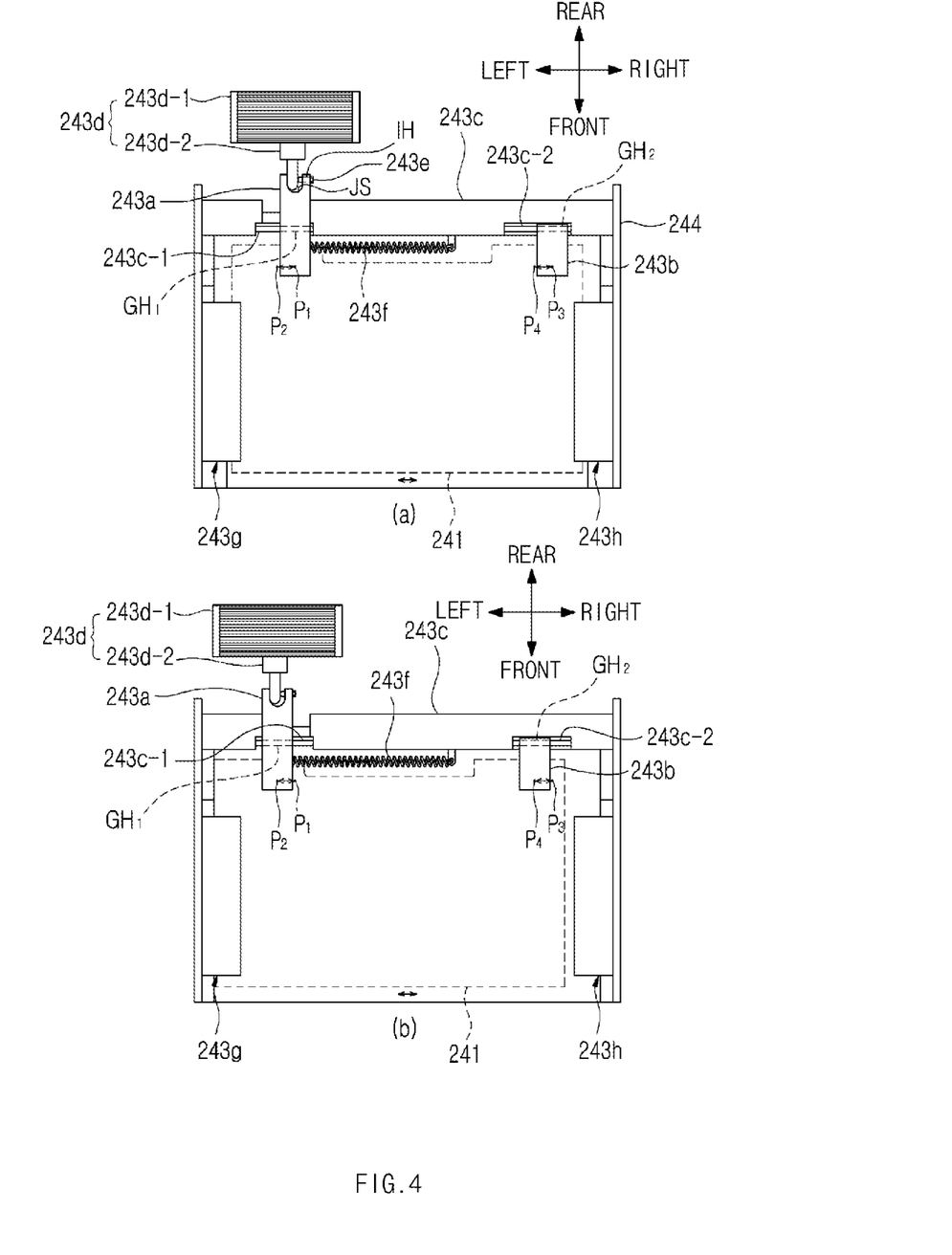
FIGS. 4A and 4B are schematic plan views of main components of the mammography of FIG. 2.

The detecting module 240 includes a grid 241, a detector 242, a moving device 243, and a case 244. For reference, FIGS. 3 to 4B illustrate a state in which a lid of the case 244 is removed.

The grid 241 attenuates a scattered radiation.

The detector 242 detects an X-ray transmitted through the grid 241.

The moving device 243 let the grid 241 reciprocate. To this end, the moving device 243 includes a first coupling member 243a, a second coupling member 243b, a guide shaft 243c, a moving source 243d, a ball plunger 243e, a tension spring 243f, and a pair of support frames 243g and 243h.

The first coupling member 243a reciprocates between a first position $P_1$ and a second position $P_2$ as illustrated in FIGS. 4A and 4B. The first coupling member 243a has a first guide hole $GH_1$ formed in a movement direction of the grid 241 and being long. A front end of the first coupling member 243a is coupled to the grid 241. In addition, the first coupling member 243a has a coupling groove JS and an installation hole IH formed at a rear end thereof. Here, the installation hole IH is formed in a lateral direction of the coupling groove JS.

The second coupling member 243b reciprocates between a third position $P_3$ and a fourth position $P_4$ as illustrated in FIGS. 4A and 4B. A distance between the third position $P_3$ and the fourth position $P_4$ is the same as that between the first position $P_1$ and the second position $P_2$. The second coupling member 243b has a second guide hole $GH_2$ formed in the movement direction of the grid 241 and being long. A front end of the second coupling member 243b is coupled to the grid 241.

The guide shaft 243c has a pair of guide bars 243c-1 and 243c-2 long in a horizontal direction. In addition, both ends of the guide shaft 243c in the horizontal direction are fixed to the case 244.

A first guide bar 243c-1 is inserted into the first guide hole $GH_1$ of the first coupling member 243a, and the second guide bar 243c-2 is inserted into the second guide hole $GH_2$ of the second coupling member 243b. Therefore, the pair of guide bars 243c-1 and 243c-2 serve to guide parts guiding reciprocation of the coupling members 243a and 243b in the horizontal direction.

The moving source 243d provides moving force to the first coupling member 243a toward the second position $P_2$. To this end, the moving source 243d includes a motor 243d-1 and a transfer member 243d-2.

The motor 243d-1 generates moving force pushing the first coupling member 243a toward the second position $P_2$. Here, the motor 243d-1 may be a linear motor or a rotating motor. The rotating motor requires a structure of converting rotating force into linear moving force. In addition, in order for the motor 243d-1 to push the first coupling member 243a only toward the second position P$_2$, power of the motor 243d-1 may be controlled or a cam may be used.

The transfer member 243d-2 has a front end inserted into the coupling groove JS of the first coupling member 243a and a rear end connected to the motor 243d-1. Therefore, the transfer member 243d-2 transfers the moving force generated in the motor 243d-1 to the first coupling member 243a.

The ball plunger 243e is installed in a form in which it is inserted into the installation hole IH of the first coupling member 243a. The ball plunger 243e acts as an elastic pressing member elastically giving pressure to the front end of the transfer member 243d-2 inserted into the coupling groove JS toward one side direction (left direction in the accompanying drawings). Therefore, the front end of the transfer member 243d-2 closely adheres to a wall surface of one side configuring the coupling groove JS without a clearance.

The tension spring 243f applies tension force to the first coupling member 243a toward the first position P$_1$. The tension spring 243f has one side fixed to the first coupling member 243a and the other side fixed to the guide shaft 243c. The tension spring may also be modified so that one side thereof is fixed to the second coupling member and the other side thereof is fixed to a fixing body (the guide shaft, a case, or the like).

Figure 5:
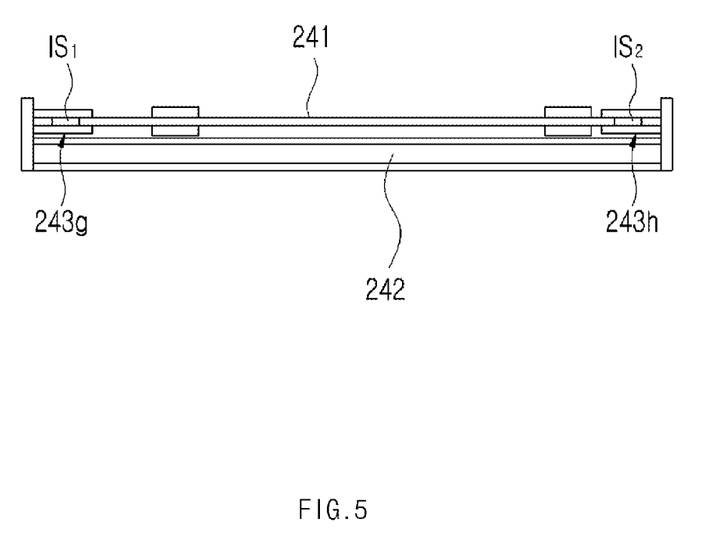
FIG. 5 is a front view of support frames used in the mammography of FIG. 2.

The pair of support frames 243g and 243h support both side portions of the grid 241 in the horizontal direction. To this end, the support frames 243g and 243h have insertion grooves IS$_1$ and IS$_2$ to which side portions of the grid 241 are inserted, respectively, as illustrated in a front view of FIG. 5. That is, a front of each of the support frames 243g and 243h has a '⊏' structure in which it is opened toward the grid 241. Due to the above-mentioned structure, both of a bottom surface and a top surface of the grid 241 are supported by the support frames 243g and 243h. The support frames 243g and 243h may be formed integrally with the case 244.

The case 244 accommodates the grid 241, the detector 242, the support frames 243g and 243h, and the like, therein.

The pressing member 250 presses the breast put on the detecting module 240. The pressing member 250 is positioned between the generator 230 and the detecting module 240. In addition, in order to press the breast and release the pressing of the breast, the pressing member 250 linearly moves between the generator 230 and the detecting module 240 (See an arrow C of FIG. 2).

Next, an operation of the mammography 200 having the configuration as described above will be described.

The breast of a patient put on the detecting module 240 for detection is pressed by the pressing member 250 in order to be photographed.

Then, the generator 230 and the detecting module 240 are operated. At this point in time, the moving device 243 is operated to let the grid 241 reciprocate, in order to remove a scattered radiation. First, in a state of FIG. 4A, the moving force by the moving source 243d is applied to the first coupling member 243a. Therefore, the first coupling member 243a, the second coupling member 243b, and the grid 241 move toward the second position P$_2$ to become a state of FIG. 4B. In addition, in the state of FIG. 4B, the moving force by the moving source 243d disappears. Therefore, the first coupling member 243a, the second coupling member 243b, and the grid 241 move toward the first position P$_1$ by the tension force of the tension spring 243f to become a state of FIG. 4A.

Figure 6:
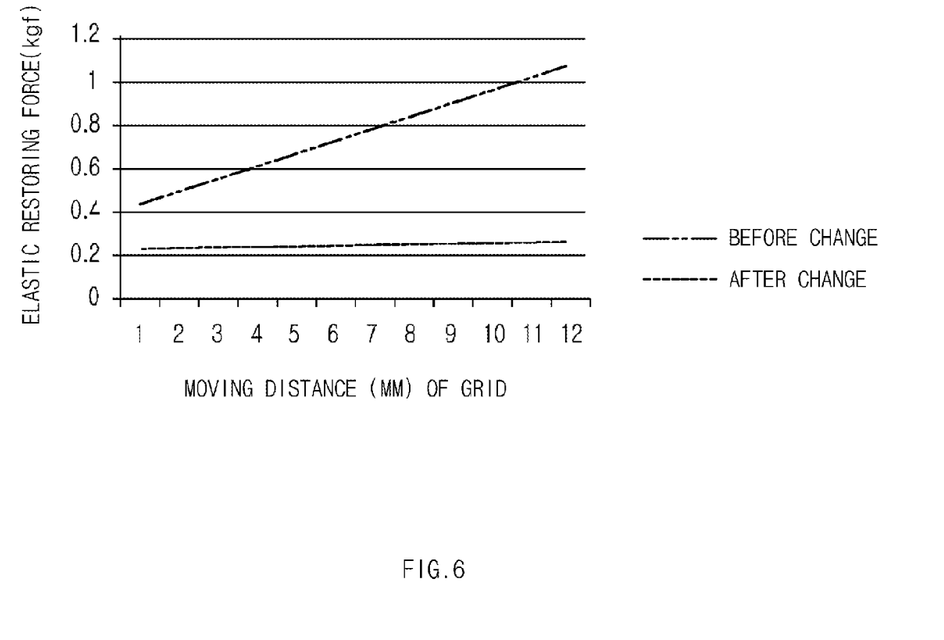
FIG. 6 is a graph for experiment data in which the related art and the present invention are compared with each other.

FIG. 6 is a graph for experiment data in which the related art and the present invention are compared with each other.

Figure 1:
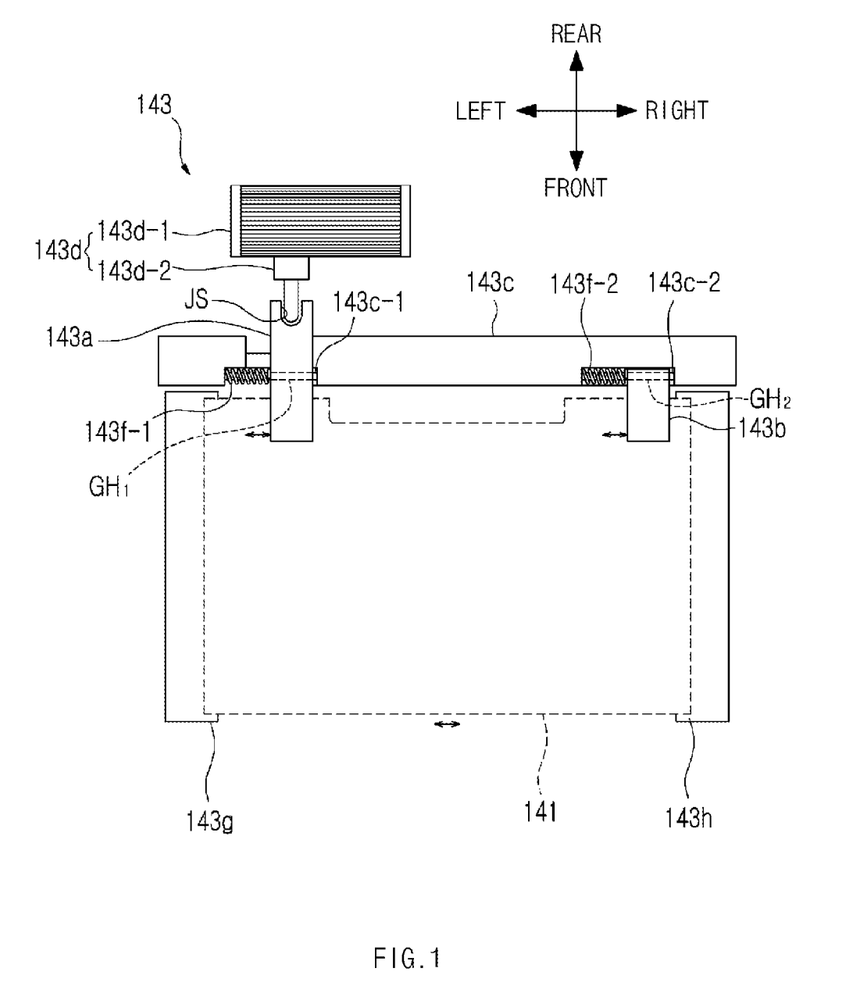
FIG. 1 is a schematic plan view of main components of an X-ray photographing apparatus according to the related art.

Referring to FIG. 6, it may be appreciated that a deviation of elastic restoring force depending on moving distances of the grids 141 and 241 becomes smaller in the case of using the tension spring 243f than in the case of using the compression springs 143f-1 and 143f-2 (See FIG. 1). Therefore, in the case of using the tension spring 243f, the grid 241 moves at a velocity closer to a constant velocity.

Figure 7:
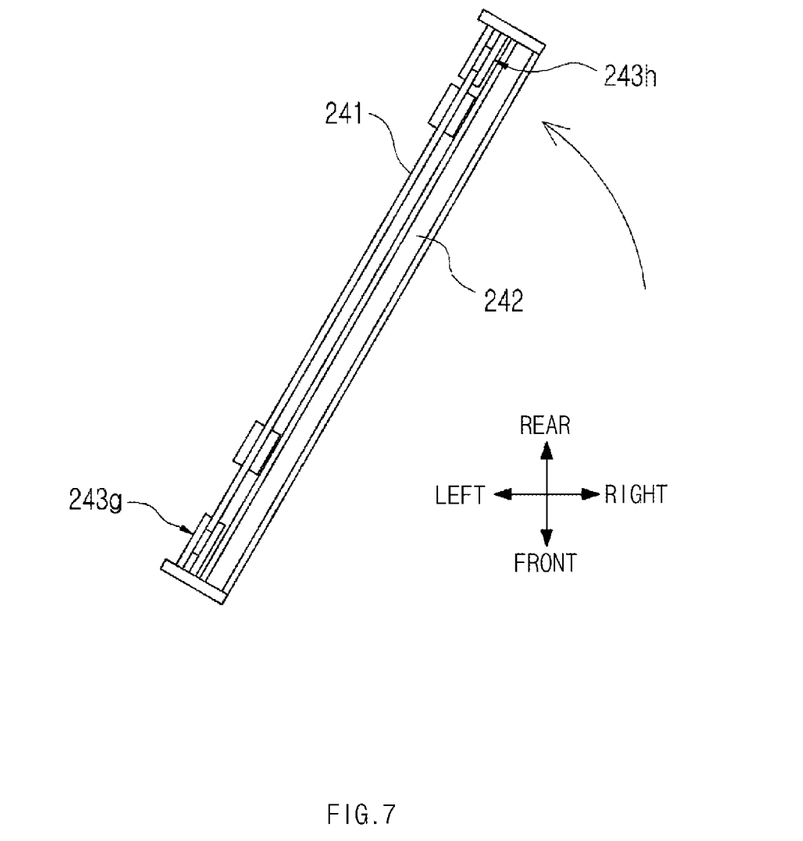
FIG. 7 is a front view of support frames used in the mammography of FIG. 2.

Meanwhile, when the C arm 220 rotates in order to change a photographing angle, the grid 241 becomes a state of FIG. 7. Even in a state in which the grid 241 stands up as illustrated in FIG. 7, the grid 241 is stably supported by the support frames 243g and 243h.

The exemplary embodiment of the present invention has been described hereinabove. Therefore, the present invention is not limited to the above-mentioned exemplary embodiment. The present invention is to be understood by the claims and an equivalent thereof.

The invention claimed is:

1. An X-ray photographing apparatus comprising:
   a generator irradiating an X-ray to a target; and
   a detecting module detecting the X-ray transmitted through the target, the detecting module including:
     a grid reciprocating between first and second positions;
     a detector detecting the X-ray transmitted through the grid; and
     a moving device causing the grid to reciprocate, the moving device including:
       a moving source providing a moving force for moving the grid from the first position to the second position;
       a tension spring providing a tension force for moving the grid from the second position to the first position;
       a coupling member connecting the moving source and the grid to each other to transfer the moving force of the moving source to the grid, wherein the coupling member has a coupling groove;
       a transfer member having a portion inserted into the coupling groove to transfer the moving force of the moving source to the coupling member; and
       a pressing member pressing the inserted portion of the transfer member to a surface of the coupling groove.

2. The X-ray photographing apparatus according to claim 1, wherein the moving device further includes
   a guide shaft including a guide part guiding reciprocation of the coupling member, and
   wherein the tension spring has one end fixed to the coupling member and the other end fixed to the guide shaft.

3. The X-ray photographing apparatus according to claim 2, wherein the guide shaft further includes a portion protruding from a surface of the guide shaft, and
   wherein the other end of the tension spring is fixed to the protruding portion of the guide shaft.

4. The X-ray photographing apparatus according to claim 1, wherein the moving device further includes at least one support frame provided with an insertion groove into which a portion of the grid is inserted so as to support the grid.

5. The X-ray photographing apparatus according to claim 1, wherein the coupling member further has an installation hole penetrating a portion of the coupling member, and
   wherein the pressing member is inserted into the installation hole.

6. The X-ray photographing apparatus according to claim 1, wherein the pressing member keeps pressing the inserted portion of the transfer member to the surface of the coupling groove when the moving device causes the grid to reciprocate.

* * * * *